United States Patent
Tolonen et al.

(10) Patent No.: US 9,254,579 B2
(45) Date of Patent: Feb. 9, 2016

(54) APPARATUS FOR PATCHING PLYWOOD VENEER

(75) Inventors: Esko Tolonen, Kajaani (FI); Erkki Kauranen, Kajaani (FI)

(73) Assignee: RAUTE OYJ, Nastola (FI)

( * ) Notice: Subject to any disclaimer, the term of this patent is extended or adjusted under 35 U.S.C. 154(b) by 1016 days.

(21) Appl. No.: 13/356,770

(22) Filed: Jan. 24, 2012

(65) Prior Publication Data

US 2012/0186700 A1     Jul. 26, 2012

(30) Foreign Application Priority Data

Jan. 25, 2011   (FI) ..................... 20115070

(51) Int. Cl.
*B27G 1/00*     (2006.01)
*G01N 21/898*   (2006.01)

(52) U.S. Cl.
CPC .............. *B27G 1/00* (2013.01); *G01N 21/8986* (2013.01)

(58) Field of Classification Search
CPC .. B27M 1/04; Y10T 29/5138; Y10T 29/5143; Y10T 29/49732; Y10T 29/49739; Y10T 29/5397; Y10T 29/49771; B23P 6/00; B23P 23/04; B23P 19/04; B23P 23/00; B27G 1/00; G01N 21/8986; G01N 21/8851

USPC ....................... 144/332, 24.16; 29/564, 564.7
See application file for complete search history.

(56) References Cited

U.S. PATENT DOCUMENTS

| 3,446,256 A | * | 5/1969 | Roberts, Jr. .............. A23N 7/01 144/2.1 |
| 3,547,170 A | * | 12/1970 | Bauer et al. ................... 144/332 |
| 4,984,172 A | | 1/1991 | Luminari |

FOREIGN PATENT DOCUMENTS

| FI | 832740 | 1/1985 |
| JP | 47-32641 | 8/1972 |
| WO | 2010124307 | 11/2010 |

OTHER PUBLICATIONS

The Finnish Search Report dated Sep. 13, 2011, corresponding to Foreign Priority No. 20115070.
JP Office Action, dated Sep. 15, 2015; Application No. 2012-011895.

\* cited by examiner

*Primary Examiner* — Matthew G Katcoff
(74) *Attorney, Agent, or Firm* — Young & Thompson

(57) ABSTRACT

A veneer patching apparatus includes a detection device for detecting and locating defect points in the veneer, a stationarily located patching unit (1/2) having a punch and a patch inserter, and elements (5, 7) for holding and conveying the veneer, controlled by the detection device. Each veneer specific patching apparatus has two or more patching units (1,2).

14 Claims, 2 Drawing Sheets

APPARATUS FOR PATCHING PLYWOOD VENEER

BACKGROUND OF THE INVENTION

1. Field of the Invention

Figure 1:
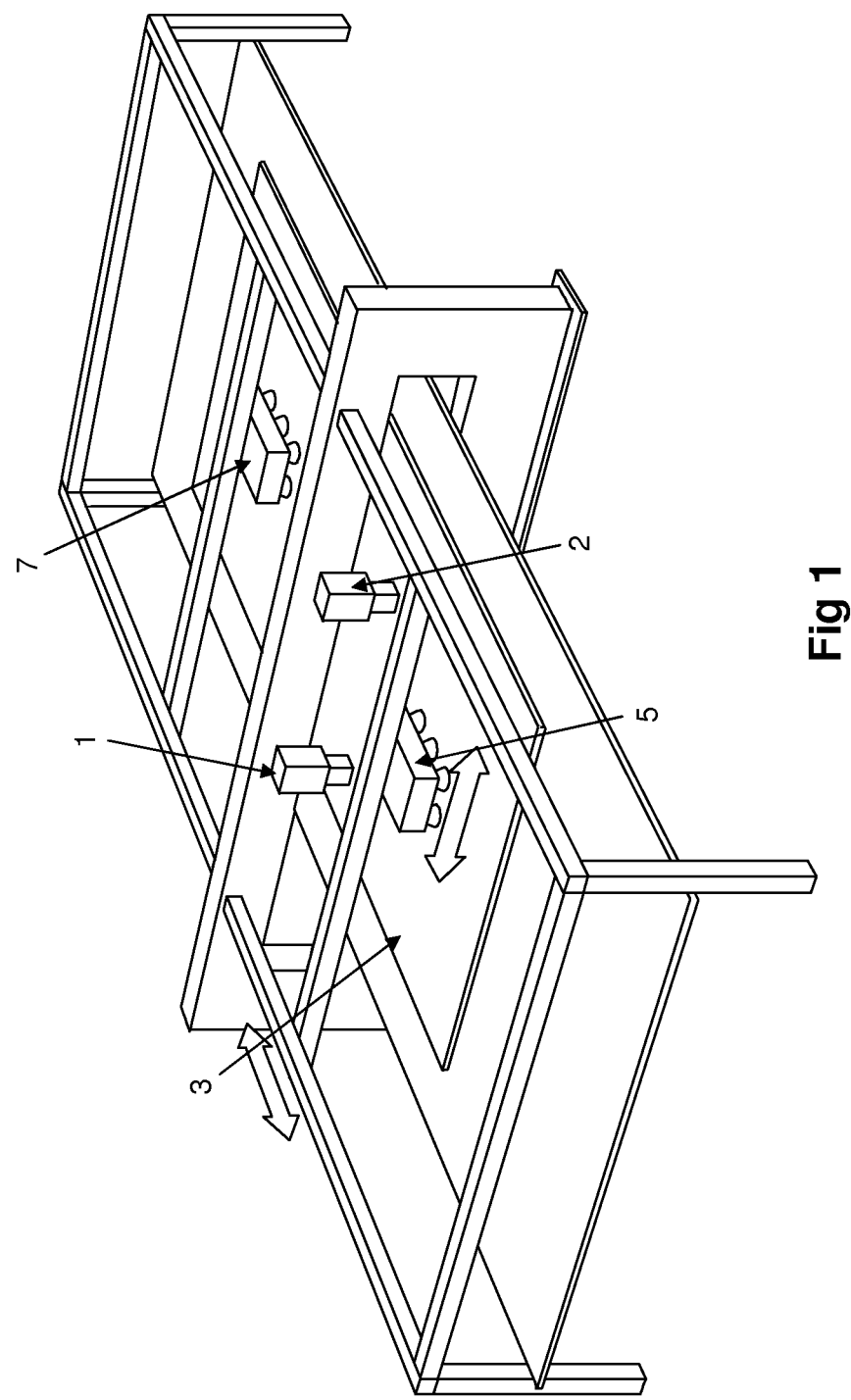

The object of the present invention is an apparatus, wherein defect points in veneer sheets coming from a dryer are patched. Prior to this processing step, the sheets have been sorted in terms of defect points so that a defect point to be patched is below a certain size.

2. Description of the Related Art

Traditionally, defect points have been patched by hand, by pressing the defect veneer point out form the sheet with a punch, and by forcing an intact veneer patch to the hole made by the punch, fitting with a tight clearance to the hole.

The patching function has also been mechanized, where the first step has been the mechanization of the punching operation and the insertion of the patch. The veneer sheet being handled has been moved by hand in to position with a patching unit, called a patching head, for carrying out the patching operation.

In further development of the mechanization, machine vision devices have been introduced, by means of which it has been possible to observe the veneer sheet's whole area for detecting defect points requiring patching. Veneer-specific information given by such a detection device has been fed to a control device, which in turn has controlled a device moving the veneer for allocating defect points in position with a patching unit. The patching spot is aligned by conveying the veneer in length-width directions, so that when the patching area approaches the midpoint of veneer's advancement, the holding function of the conveying device is moved over the patching apparatus to an area of the veneer having passed patching.

SUMMARY OF THE INVENTION

The veneer sheets being handled are rather large in size, for example the length being 8 feet (approx. 2.6 m) and the width being half of this measure. A veneer spot mendable by patching is maximized in the sorting of the veneer for decreasing quality loss, which sets high requirements in aligning veneers precisely in position with the patching unit. In addition, alignment from one patching spot to another should be made to happen rapidly. Fulfilling these objects with a veneer having a structure yielding to some extent requires compromises from the operation of the apparatus. Veneer has to be allowed to settle after each transfer braking, so that the patching target point sets closely to the desired position in respect to the patching unit. The need for a compromise between speed and accuracy has substantially diminished with an apparatus according to the present invention, which is characterized in that each veneer-specific patching apparatus has two or more patching units.

BRIEF DESCRIPTION OF THE DRAWING FIGURES

The invention is explained in detail by means of the attached drawing, wherein

FIG. 1 shows an illustration of a veneer patching apparatus according to the invention, and FIGS. 2A to 2D the gradual phased pattern in the advancing direction of the veneer of holding devices included in the apparatus.

DETAILED DESCRIPTION OF THE INVENTION

Concerning the conveying of the veneer, the apparatus shown in FIG. 1 is implemented in two pieces in the advancing direction of the veneer, and is equipped with two holding devices 5, 7, the other one operating on the leading side of the apparatus, and the other one on the trailing side. The veneer sheet 3 to be handled enters the patching apparatus advancing in a longitudinal direction. The patching units 1 and 2 have been stationarily fixed substantially in the middle of the apparatus in the advancing direction of the veneer sheet. The presumed initial position for the patching units 1 and 2 is locating them at ¼ and ¾ of the width of the veneer sheet. The implementation of the holding devices' conveying means may naturally require another positioning when optimizing the programmatic conveying function.

Figure 2B:
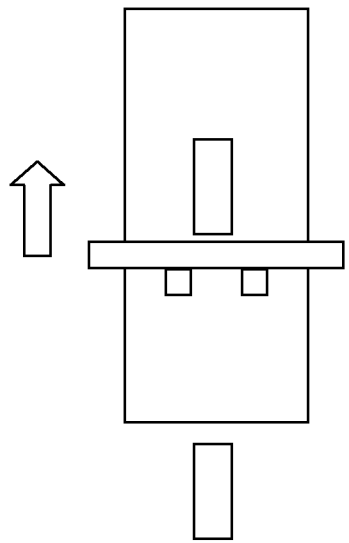
Figure 2D:
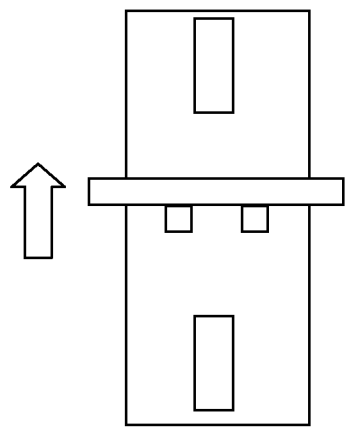
Figure 2A:
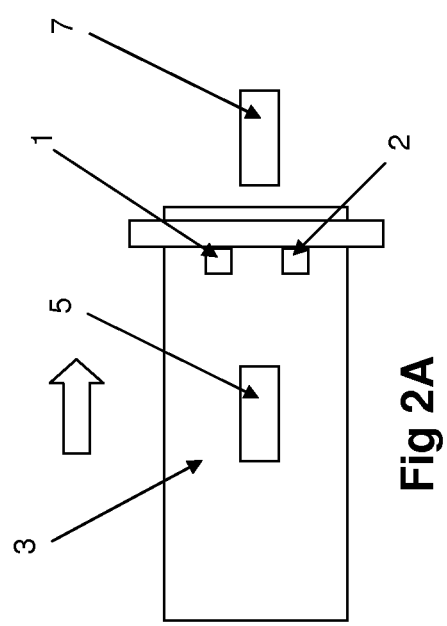
Figure 2C:
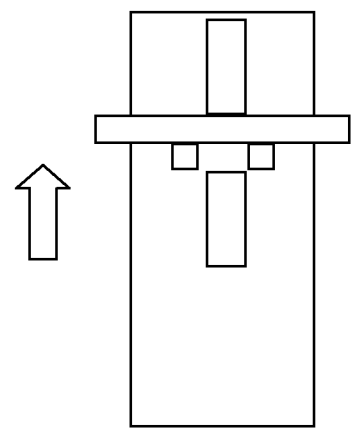

After the veneer sheet, supported by a suitable conveyor, has entered the apparatus, it is then grabbed with a holding device 5, for example with a suction grabber substantially at the mid-section of the sheet as illustrated (FIG. 2A). Before entering the patching apparatus, the veneer sheet has been exposed to a detection device, a machine vision device acting as a scanner, the defect point information given by it is stored sheet-specifically for the control of the holding devices' conveying means moving the sheet in the patching apparatus. The control commands the holding devices' conveying means (such as crossing carriages) so that each time a defect point sets according to the most appropriate transfer distance either in position with patching unit 1 or 2. The command's transfer path is optimized to be as short as possible.

The mutual operation of the holding devices 5, 7 is synchronized so that the veneer sheet undergoing the patching operation is always supported by either one of the holding devices, both acting on their own sides of the apparatus. In a situation according to FIG. 2B, the veneer sheet has advanced in to a situation where the trailing side holding device 7 has met the veneer sheet in the advancing direction, and the sheet is supported by both of the holding devices. In the next phase (FIG. 2C), the leading side holding device 5, detached from the veneer sheet, moves to a receiving position of a new veneer sheet, in which position it continues to support the veneer sheet 3 undergoing the patching operation. In the next phase (FIG. 2D), the veneer sheet has advanced to be supported solely by the trailing side holding device 7, and travels supported by it for the rest of the patching operation to be removed from the apparatus. The reciprocal transitions of the holding devices are synchronized so that the veneer sheet being patched is constantly supported and the patching operation can continue without interruptions, as well as removing a patched veneer sheet and introducing a new one runs substantially as a continuous operation.

Conventional patching units have a holding function to keep the veneer in place during the punching and patch insertion. The patching units 1 and 2 can be implemented so that in addition to the punching function used for patching, they have a function with which they can be used for holding the veneer sheet without damaging the veneer sheet. This can be done by controlling the holding function independently from the punching and patch insertion functions. This function is relevant in situations where the defect point to be patched happens to be in position with or under a holding device 5 or 7 so that the patching apparatus is unable to function unless the holding device is moved out of the way. The unit executing the patching functions normally, the other unit has been given a command for holding.

With two patching units, the transfer distance transverse to the veneer's advancing directions is halved, as a result of which the floor space required by the patching line is also substantially reduced. Additionally, reducing the transfer distance has clearly better pre-requisites for carrying out automation than with longer transfer distances. A short transfer distance also creates a clearly higher production capacity.

Instead of the two patching units presented, the apparatus can have even more veneer specific patching units, through which the operation of the apparatus can be even further accelerated while maintaining accuracy.

The invention claimed is:

1. A patching apparatus for plywood veneer, the apparatus comprising:
   a detection device for detecting and locating defect points in the veneer;
   two or more stationary patching units, each patching unit having a punch and a patch inserter; and
   at least two holding devices configured for holding and conveying the veneer in advancing and transversal directions of a veneer sheet, controlled by the detection device,
   wherein the two or more patching units are positioned to locate substantially in a middle of the apparatus in the advancing direction of the veneer sheet.

2. The patching apparatus according to claim 1, wherein the patching units are located at approximately ¼ and ¾ of a width of the veneer sheet.

3. The patching apparatus according to claim 1, wherein the patching units have a punch function and a controlled holding function.

4. The patching apparatus according to claim 1, wherein there are two holding devices located functionally in the advancing direction of the veneer sheet.

5. The patching apparatus according to claim 1, wherein travels paths of the at least two holding devices are optimized according to information given by the detection device.

6. The patching apparatus according to claim 2, wherein the patching units have a punch function and a controlled holding function.

7. The patching apparatus according to claim 2, wherein there are two holding devices located functionally in the advancing direction of the veneer sheet.

8. The patching apparatus according to claim 2, wherein travels paths of the at least two holding devices are optimized according to information given by the detection device.

9. The patching apparatus according to claim 3, wherein there are two holding devices located functionally in the advancing direction of the veneer sheet.

10. The patching apparatus according to claim 3, wherein travels paths of the at least two holding devices are optimized according to information given by the detection device.

11. The patching apparatus according to claim 1, wherein each holding device comprises a suction grabber.

12. The patching apparatus according to claim 1, wherein the detection device comprises a machine vision device acting as a scanner.

13. The patching apparatus according to claim 1, wherein conveying devices convey the holding devices.

14. The patching apparatus according to claim 1, wherein conveying devices comprising crossed carriages convey the holding devices.

* * * * *